(12) United States Patent
Kuo et al.

(10) Patent No.: US 6,288,233 B1
(45) Date of Patent: Sep. 11, 2001

(54) ENANTIOSELECTIVE ALKYLATION OF TRICYCLIC COMPOUNDS

(75) Inventors: Shen-Chun Kuo, Union; Frank Xing Chen, Plainsboro, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/667,411

(22) Filed: Sep. 21, 2000

Related U.S. Application Data

(62) Division of application No. 09/442,511, filed on Nov. 18, 1999
(60) Provisional application No. 60/109,148, filed on Nov. 20, 1998.

(51) Int. Cl.[7] .................................................. C07D 221/06
(52) U.S. Cl. ............................................................. 546/93
(58) Field of Search ................................................ 546/93

(56) References Cited

U.S. PATENT DOCUMENTS

| 5,712,280 | * | 1/1998 | Doll | 514/253 |
| 5,874,442 | * | 2/1999 | Doll | 514/290 |

FOREIGN PATENT DOCUMENTS

| WO 93/21176 | 10/1993 | (WO) . |
| WO 95/10516 | 4/1995 | (WO) . |
| WO 96/30363 | 10/1996 | (WO) . |
| WO 96/31478 | 10/1996 | (WO) . |
| WO 97/23478 | 4/1997 | (WO) . |

OTHER PUBLICATIONS

Gauthier, Sylvain, et al., "(S)-(+)-4-[7-(2,2-Dimethyl-1-oxopropoxy)-4-methyl-2-[4-[2-(1-piperidinyl)-ethoxy]phenyl]2H-1-benzopyran-3-yl]-phenyl 2,2-Dimethylpropranoate (EM-800): A Highly Potent, Specific, and Orally Active Nonsteroidal Antiestrogen," *J. Med. Chem.*, vol. 40, pp. 2117–2122 (1997).

Sato, Kaisaku, et al., "Stereoselective Reactions. 26. Solution Structures of a Chiral Bidentate Lithium Amide in Relation to The Solvent–Dependent Enantioselectivities in Deprotonation Reaction," *Tetrahedron*, vol. 53, No. 21, pp. 7191–7200 (1997).

(List continued on next page.)

*Primary Examiner*—Evelyn Mei Huang
(74) *Attorney, Agent, or Firm*—Arthur Mann; Margaret M. Albanese; William Y. Lee

(57) ABSTRACT

Disclosed is a process for preparing a compound of the formula:

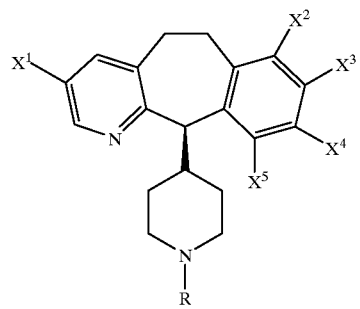

(I)

wherein $X^1$, $X^2$, $X^3$, $X^4$, and $X^5$ are independently selected from the group consisting of H, halo, alkyl, alkoxy, aryl, and aryloxy, and R is a protecting group, in which a compound having the formula

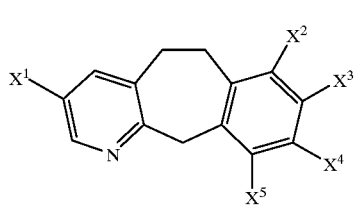

(II)

wherein $X^1$, $X^2$, $X^3$, $X^4$, and $X^5$ are as defined above, is treated with the following, in any sequence:

(a) a non-nucleophilic strong base;
(b) a chiral amino alcohol; and
(c) a compound having the formula

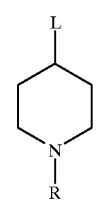

(V)

wherein L is a leaving group and R is as defined above. The compounds made by this process are useful intermediates for preparing compounds that are inhibitors of farnesyl protein transferase. Also disclosed is a compound having the formula:

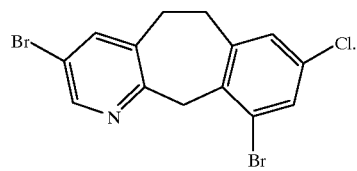

1 Claim, No Drawings

OTHER PUBLICATIONS

Gallagher, D.J., et al., "Chiral Organolithium Complexes: The Structures of β–Lithiated β–Phenylcarboxamides and the Mechanism of Asymmetric Substitution in the Presence of (–)–Sparteine," *J. Am. Chem. Soc.*, vol. 118, pp. 11391–11398 (1996).

Weisenburger, Gerald A., et al., "α–Lithiation of N–(tert-Butoxycarbonyl)–N–(p–methoxyphenyl)allylamines Mediated by (–)–Sparteine: Enantioselective Synthesis of Either Enantiomer of 3–Substituted Enecarbamates," *J. Am. Chem. Soc.*, vol. 118, pp. 12218–12219 (1996).

Hoppe, D., et al., "Heteroatom–directed lithiations of chiral aklyl carbamates: A powerful tool for enantioselective synthesis," *Pure & Appl. Chem.*, vol. 68, No. 3, pp. 613–618 (1996).

Hoppe, I., et al., "Generation of Enatiomerically Enriched Lithium Indenides by Means of (–)–Sparteine: Structure, Stereoselective Substitution, and Solvent Effects," *Angew. Chem. Int. Ed. Engl.*, vol. 34, No. 19, pp. 2158–2160 (1995).

Gawley, Robert E., et al., "Alkylation of 2–Lithio–N–Methylpiperidines and –pyrrolidines: Scope, Limitations, and Stereochemistry," *J. Org. Chem.*, vol. 60, pp. 5763–5769 (1995).

Enders, Dieter, et al., "A Convenient Enantioselective Synthesis of (R)–(–)–Phoracantholide I, a Component of the Defensive Secretion of the Eucalypt Longicorn *Phoracantha synonyma,*" *Liebigs Ann.*, pp. 1127–1128 (1995).

Evans, etal., "(S)–4–Benzyl–2–oxazolidinone," *Encyclopedia of Reagents for Organic Synthesis*, vol. 1, pp. 345–356 (1995).

Koga, Kenji, "Asymmetric synthesis mediated by chiral ligands," *Pure & Appl. Chem.*, vol. 66, No. 7, pp. 1487–1492 (1994).

*Chemical Abstracts*, vol. 121, No. 7, Abstract No. 82181, XP002130992, Faber, et al., "Catalytic kinetic resolution of 5–alkoxy–2(5H)–furanones," *Tetrahedron*, vol. 50, No. 16, pp. 4775–4794 (1994).

O'Donnell, et al., "A New Active Catalyst Species for Enantioselective Alkylation by Phase–Transfer Catalysts," *Tetrahedron*, vol. 50, No. 15, pp. 4507–4518 (1994).

Gant, et al., "The Chemistry of 2–Oxazolines (1985–Present)," *Tetrahedron*, vol. 50, No. 8, pp. 2297–2360 (1994).

Heaton, et al., "Chiral Arene Chromium Tricarbonyl Complexes as Enantioselective Catalysts: Highly Selective 1,2 Alkyl Additions to Adehydes," *Tetrahedron Letters*, vol. 33, No. 13, pp. 1693–1696 (1992).

Papasergio, et al., "Lithiation of 2–Me$_3$SiCHRC$_5$H$_4$NR=H or SiMe$_3$): Influence of Solvent on the Nature of the Product (from X–Ray Structure Determinations)† and Asymmetric Induction. A Note on the Lithiation of Some Analogous 3– and 4– Methylpyridines," *J. Chem. Soc. Dalton Trans.*, pp. 1161–1172 (1990).

Tomioka, et al., "Asymmetric α–Alkylation of Cyclohexanone by Mediation of a Chiral Ligang and the Leaving-Group Effect of Electrophiles on Enantioselectivity," *Chem. Pharm. Bull.*, vol. 37, No. 4, pp. 1120–1122 (1989).

Hughes, et al., "Efficient Catalytic Asymmetric Alkylations. 3.[1] A Kinetic and Mechanistic Study of the Enantioselective Phase–Transfer Methylation of 6,7–Dichloro–5–methoxy–2–phenyl–1–indanone," *J. Org. Chem*, vol. 52, pp. 4745–4752 (1987).

*Chemical Abstracts*, vol. 116, No. 19, Abstract No. 194813, XP–002130993, Ahmad, et al., "Inhibition of pig kidney L–aromatic amino acid decarboxylase by 2,3–methano–m–tyrosines," *Journal of Medicinal Chemistry*, vol. 35, No. 8, pp.1410–1417 (1992).

*Chemical Abstracts*, vol. 95, No. 15, Abstract No. 128976, XP–002130994, Kajiwara, et al., "Stereoselective synthesis of ectocarpene and its antipode via microbiological asymmetric hydrolysis," *Agric. Biol. Chem.*, vol. 45, No. 6, pp. 1461–1466 (1991).

*Chemical Abstracts*, vol. 82, No. 17, Abstract No. 111993, XP–002130995, Gustafsson, et al., "New .alpha.–(Cyclopolymethylene–2–pyrazolyl) propionic acids. Resolution of .alpha.–(cyclohepta–2–pyrazolyl) propionic acid and determination of its absolute configuration," *Acta Chem. Scand. Ser. B*, vol. B28, No. 9, pp. 1069–1073 (1974).

Villani, et al., "Derivatives of 10,11–Dihydro–5H–dibenzo [a,d]cycloheptene and Related Compounds. 6. Aminoalkyl Derivatives of the Aza Isoteres†," *Journal of Medicinal Chemistry*, vol. 15, No. 7, pp. 750–754 (1972).

Nozaki, et al., "Asymmetric Syntheses by Means of (–)–Sparteine Modified Organometallic Reagents," *Tetrahedron*, vol. 27, pp. 905–913 (1971).

King, Harold, "Conversion of Hydroquinidine into Hydrocinchonine and of Cupreine into Cinchonidine," *J. Chem Soc.*, pp. 523–524 (1946).

Renfew, et al., "Cinchona Alkaloids in Pneumolnia. XII. Derivative of 6'–Amino–apocinchonidine," *J. Am. Chem. Soc.*, vol. 65, pp. 2309–2310 (1943).

* cited by examiner

ENANTIOSELECTIVE ALKYLATION OF TRICYCLIC COMPOUNDS

This application is a divisional of U.S. Ser. No. 09/442,511, filed on Nov. 18, 1999, which claims the benefit of U.S. Provisional Application No. 60/109,148, filed November 20, 1998.

BACKGROUND OF THE INVENTION

This invention provides a process for preparing intermediates useful in the preparation of tricyclic compounds known as inhibitors of farnesyl protein transferase. In particular, the compounds prepared by the process of this invention are useful as chiral intermediates in the preparation of chiral compounds that are FPT inhibitors such as those disclosed in PCT Publication No. WO97/23478, published Jul. 3, 1997.

Over the last few decades a number of enantioselective carbon-carbon bond forming reactions have been developed that fall into two distinct groups - those that involve alkylations of a covalently bonded chiral precursor and those that use a non-covalently bonded chiral auxiliary. Examples of the former include Evan's oxazolidinone system, Meyer's oxazoline system and Enders' RAMP/SAMP systems. (See Evans, D. A., et al., *Encyclopedia of Reagents for Organic Synthesis*; Wiley: Chichester, 1995, Vol. 1, p. 345; Gant, T. G.; Meyers, A. I. *Tetrahedron* 1994, 50, 2297; and Enders, D. et al, *Liebigs Ann.* 1995, 1127.) Examples of the latter, include alkylations of stabilized anions of ketones, imines, amino acid derived Schiff bases, N-alkyl carbamates and O-alkyl carbamates that are stabilized using non-covalently bonded chiral alkaloid bases or chiral lithium bases. (See, e.g., Hughes, D. L., et al, *J. Org. Chem.* 1987, 52, 4745.; Sato, D. et al, *Tetrahedron* 1997, 53, 7191; Koga, K. *Pure & Appl. Chem.* 1994, 66, 1487; Tomioka, K. et al, *Chem. Pharm. Bull.* 1989, 37, 1120; O'Donnell, M. J., et al, *Tetrahedron* 1994, 50, 4507; Weisenburger, G. A. et al, *J. Am. Chem. Soc.* 1996, 118, 12218; Gallagher, D. J. et al, *J. Am. Chem. Soc.* 1996, 118, 11391; and Hoppe, D. et al, *Pure & Appl. Chem.* 1996, 68, 613.) These reactions are similar in that the anion that is generated and alkylated has an adjacent carbonyl-type stabilizing group such as a ketone, imine or hydrazone. There have been few examples of a non-carbonyl type group stabilized anion. Gawley reported that an α-aminoorganolithium anion generated from a chiral stannane precursor is configurationally stable, and although alkylation with primary alkyl halides affords products with excellent enantioselectivity in certain cases, the fact that the chiral stannane precursor must be resolved detracts from this procedure. (See Gawley, R. E., et al, *J. Org. Chem.* 1995, 60, 5763.) Noyori et al. reported that silylation and carboxylation of the anion of the ethyl benzene/(-)-sparteine complex proceeds in ≈30% enantiomeric excess (e.e.) with low yields and significant amounts of reaction on the aromatic nucleus was also observed. (See Nozaki, H.; Aratani, T.; Toraya, T.; Noyori, R. *Tetrahedron* 1971, 27, 905.) White et al. reported that methylation of a 2-methylpyridine/(-)-sparteine complex proceeds in 20% e.e. and 64% yield. (See Papasergio, R. I.; Skelton, B. W.; Twiss, P.; White, A. H.; Raston, C. L. *J. Chem. Soc. Dalton Trans.* 1990, 1161.) Hoppe et al. reported that acylation of an indenine system (allylic anion) proceeded in >95% ee with 52–79% yields. (See Hoppe, I. et al, *Agnew. Chem. Int. Ed. Engl.* 1995, 34, 2158.)

We have now discovered a process for the enantioselective alkylation of non-ketone/amide/carbamate/imine benzyl type methylene compounds utilizing a chiral amino alcohol as a chiral ligand that results in high e.e. and high yield of intermediates useful for preparing the chiral FPT inhibitors discussed above.

SUMMARY OF THE INVENTION

This invention provides a process for preparing a compound of the formula:

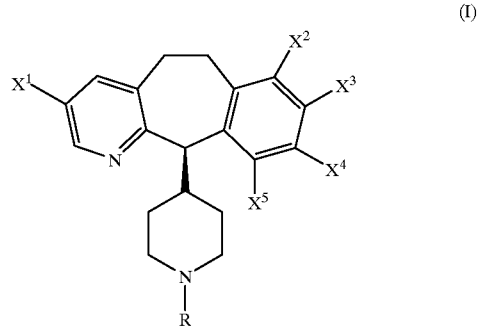

(I)

wherein $X^1$, $X^2$, $X^3$, $X^4$, and $X^5$ are independently selected from the group consisting of H, halo, alkyl, alkoxy, aryl, and aryloxy, and R is a protecting group, said process comprising:

treating a compound having the formula

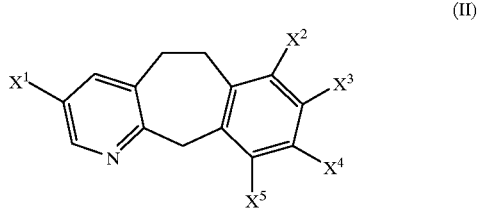

(II)

wherein $X^1$, $X^2$, $X^3$, $X^4$, and $X^5$ are as defined above, with the following, in any sequence:

(a) a non-nucleophilic strong base;
(b) a chiral amino alcohol; and
(c) a compound having the formula

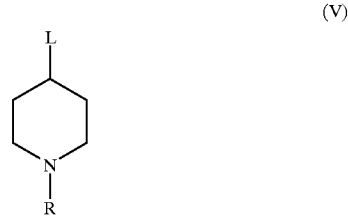

(V)

wherein L is a leaving group and R is as defined above.

Also claimed herein is a process for preparing a compound having the formula

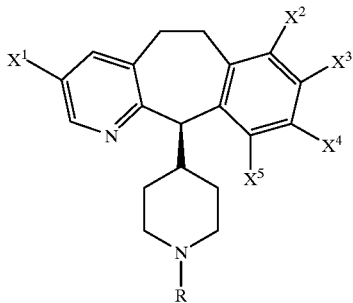

wherein $X^1$, $X^2$, $X^3$, $X^4$, and $X^5$ are independently selected from the group consisting of H, halo, alkyl, alkoxy, aryl, and aryloxy, and R is a protecting group, said process comprising:

(a) reacting a compound having the formula

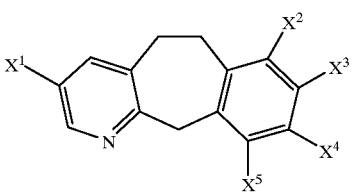

wherein $X^1$, $X^2$, $X^3$, $X^4$, and $X^5$ are as defined above, with a non-nucleophilic strong base in the presence of a chiral amino alcohol to form a complex; and (b) reacting the complex formed in step (a) with a compound having the formula

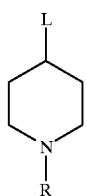

wherein L is a leaving group and R is as defined above.

DETAILED DESCRIPTION

As used herein, the term "alkyl" means straight or branched hydrocarbon chain groups having 1 to 6 carbon atoms.

"Halo" means fluorine, chlorine, bromine or iodine radicals.

"Alkoxy" refers to groups having the formula —OR, wherein R is alkyl.

"Aryl" refers to a carbocyclic group having at least one aromatic ring.

"Aryloxy" refers to a group having the formula —OR, wherein R is aryl.

"e.e." represents the percentage obtained by subtracting the amount of the S-enantiomer from the R-enantiomer, and dividing by the sum of the amount of R-enantiomer and S-enantiomer:

e.e. %=100×(R-enantiomer−S-enantiomer)/(R-enantiomer+S-enantiomer).

The following abbreviations are used herein: "Boc" refers to tert-butoxy carbonyl; "LDA" refers to lithium diisopropylamide; "THF" refers to tetrahydrofuran; and "Ph" refers to a phenyl group.

The compounds prepared by the process disclosed above are useful as intermediates for preparing chiral compounds that are FPT inhibitors, such as those disclosed in PCT Publication No. WO97/23478, published Jul. 3, 1997. Such compounds may be prepared by deprotecting the compound of formula (I), i.e., removing the R group by treatment with acid (e.g., $H_2SO_4$) to form the free amine, or optionally reacting the free amine with a suitable acid (e.g., N-acetyl-L-phenylalanine) to form a stable salt, and acylating the free base or the salt with the desired acyl group to form the desired FPT inhibitor. The compounds prepared by the process of the present invention are particularly useful for preparing the following compound:

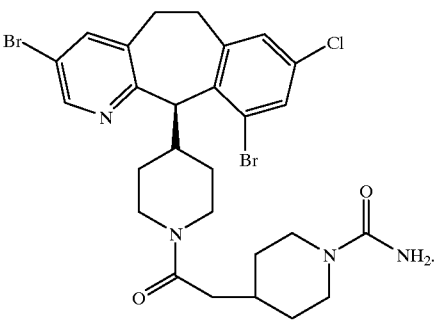

Preferably, $X^1$, $X^2$, $X^3$, $X^4$, and $X^5$ are selected from H or halo. More preferably, $X^2$ and $X^4$ are H, and $X^1$, $X^3$ and $X^5$ are halo. Halo is most preferably Cl or Br. Most preferably, $X^1$ is Br, $X^2$ is H, $X^3$ is Cl, $X^4$ is H, and $X^5$ is Br.

Non-limiting examples of leaving groups, L, include sulfonates (e.g., mesylate, tosylate, closylate (para-chloro tosylate), and brosylate (para-bromo tosylate)), phosphates (e.g., alkyl phosphates, such as diethyl phosphate), benzoates, and halo. Preferably, the leaving group, L, is a sulfonate, more preferably, mesylate or tosylate.

The protecting group may be any group suitable for protecting the nitrogen atom of the piperidine ring. Non-limiting examples of protecting groups include sulfonates, and acyl groups, e.g., tert-butoxycarbonyl (BOC),

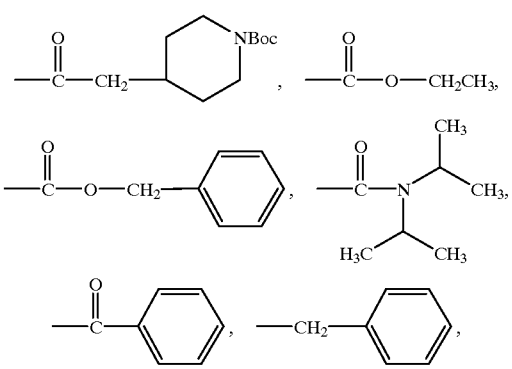

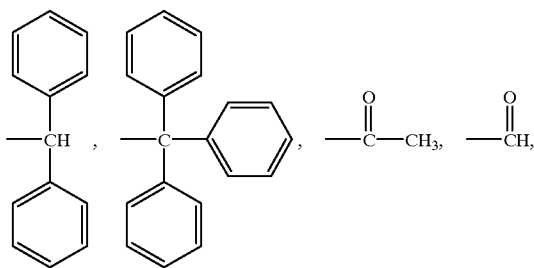
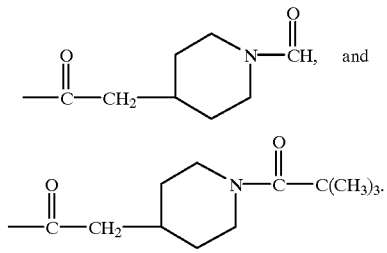
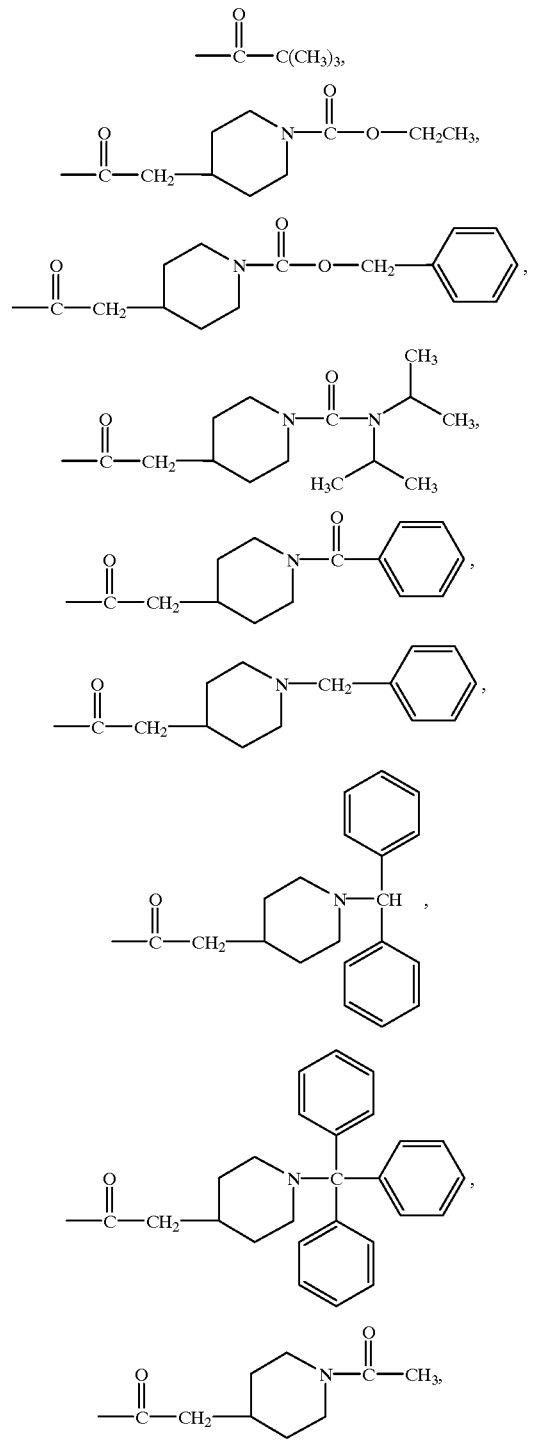
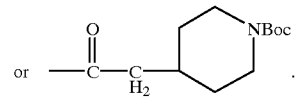

Preferably, the protecting group is an acyl group, more preferably, tert-butoxycarbonyl

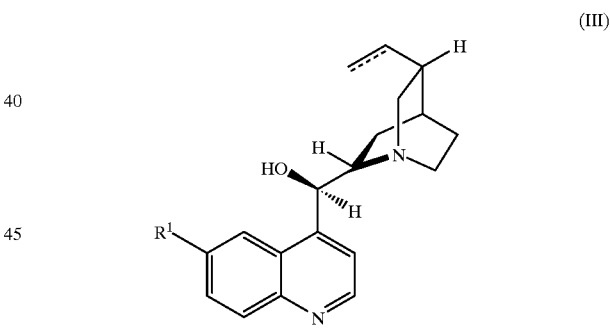

Examples of suitable non-nucleophilic strong bases include, but are not limited to, lithium duisopropylamide (LDA), lithium 2,2,6,6-tetramethylpiperidine, 1-lithium 4-methylpiperazide, 1,4-dilithium piperazide, lithium bis (trimethylsilyl) amide, sodium bis(trimethylsilyl)amide, potassium bis(trimethylsilyl)amide, isopropyl magnesium chloride, phenyl magnesium chloride, lithium diethylamide, and potassium tert-butoxide. Preferably, the non-nucleophilic strong base is LDA.

Non-limiting examples of chiral amino alcohols include quinine and quinine derivatives, 1,2- and 1,3-aminoalcohol derivatives, and quinoline alcohol derivatives.

Preferably, the chiral amino alcohol is a compound (i) having the formula (III)

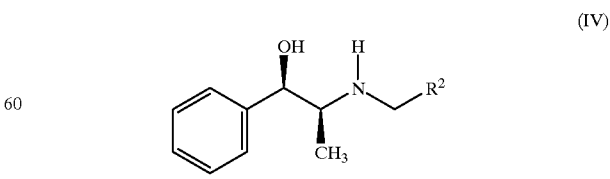

wherein the dotted line represents an optional second bond and wherein $R^1$ is selected from alkoxy, aryloxy, or $NR^A R^B$, wherein $R^A$ and $R^B$ are selected from alkyl or aryl, $R^1$ being optionally substituted by one or more alkoxy groups, or (ii) having the formula (IV)

wherein $R^2$ is a phenyl group optionally substituted by 1 to 5 substituents independently selected from the group consisting of alkyl and alkoxy.

The chiral amino alcohol of formula (III), above, is quinine, or a quinine derivative. Non-limiting examples of chiral amino alcohols of formula (III) include

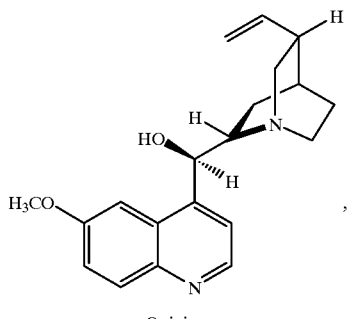

Quinine

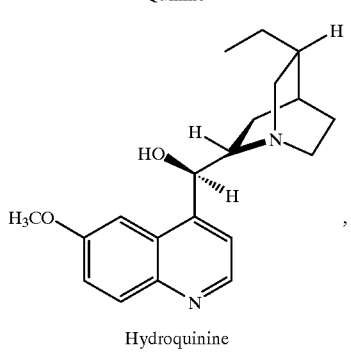

Hydroquinine

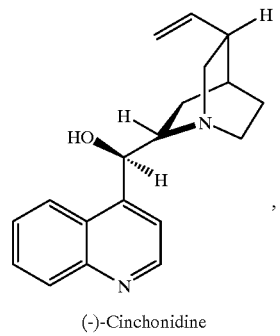

(-)-Cinchonidine

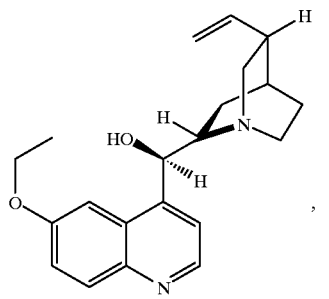

,

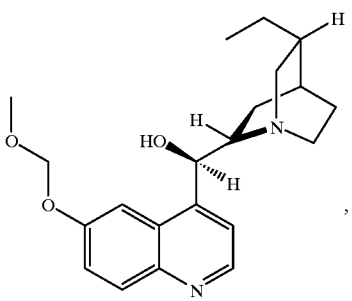

,

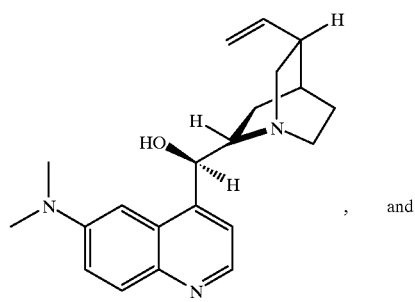

, and

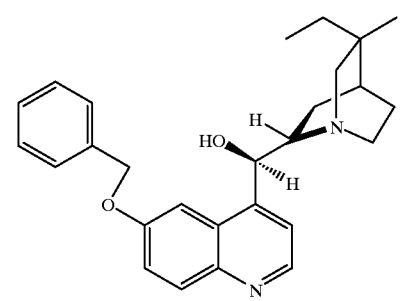

.

Preferably, $R^1$ in formula (III) is alkoxy. The chiral amino alcohol of formula (III) is most preferably selected from quinine, hydroquinine,

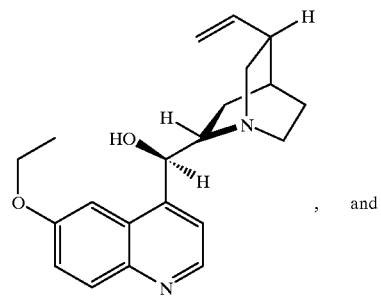

, and

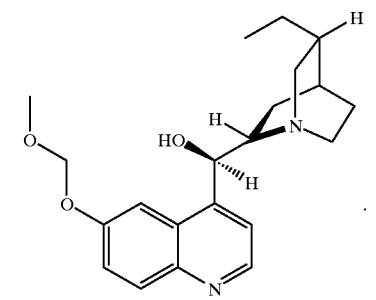

.

Quinine is especially preferred.

The chiral amino alcohol of formula (IV) is a derivative of norephedrine. Preferably, $R^2$ is phenyl substituted with 1–3 alkoxy substitents. Preferably, the alkoxy substituents are methoxy or ethoxy, with methoxy being particularly preferred. Non-limiting examples of chiral amino alcohols of formula (IV) include:

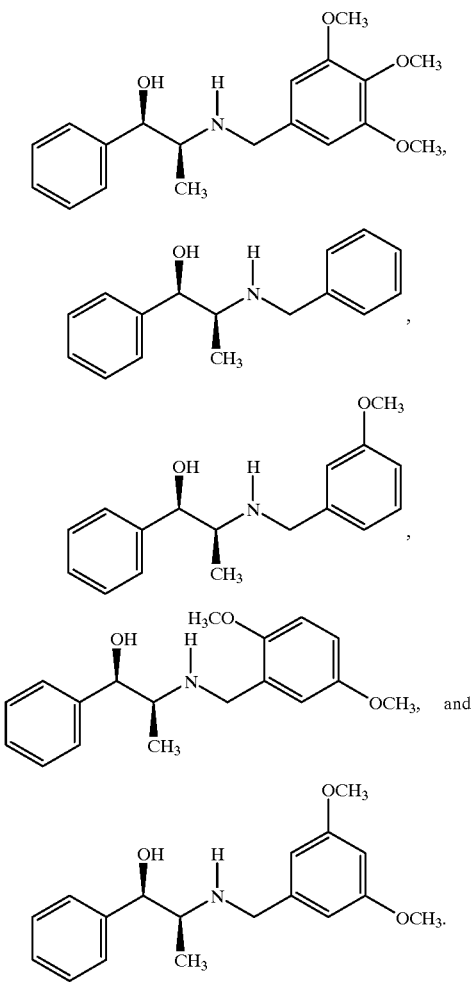

The chiral amino alcohol of formula (IV) is most preferably

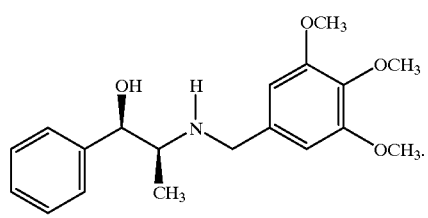

It is believed that the process claimed herein proceeds according to the following mechanism: The base accepts a proton from the tricyclic compound of formula (II), forming an anion:

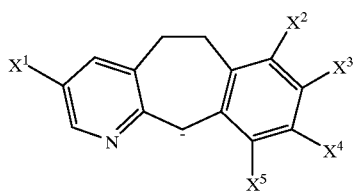

The tricyclic anion subsequently forms a complex with the chiral amino alcohol and the base. The tricyclic anion of the complex reacts with the piperidine compound of formula (V), displacing the leaving group L, thereby forming the desired compound of formula (I).

The process of our invention is preferably carried out in an organic solvent. Suitable organic solvents, include, but are not limited to non-protic organic solvents, e.g., toluene, benzene, cyclohexane, tetrahydrofuran, anisole, chlorobenzene, and mixtures thereof. Toluene is a particularly preferred solvent.

The process is preferably carried out at a temperature range of from −20° C. to +60° C., more preferably, at a temperature range of from −10° C. to +40° C., most preferably, at a temperature range of from 0° C. to +25° C.

The amount of non-nucleophilic strong base used preferably ranges from 3.0 to 5.0 equivalents, more preferably 3.0 to 4.0 equivalents, most preferably 3.0 to 3.6 equivalents.

The amount of the chiral amino alcohol used preferably ranges from 1.0 to 2.0 equivalents, more preferably 1.0 to 1.5 equivalents, most preferably 1.0 to 1.3 equivalents.

The amount of the piperidine compound of formula (V) used preferably ranges from 1.0 to 2.0 equivalents, more preferably 1.0 to 1.5 equivalents, most preferably 1.0 to 1.3 equivalents.

As noted above, the tricyclic starting compound may be treated with the non-nucleophilic strong base, the chiral amino alcohol, or the piperidine compound of formula (V) in any order, including mixtures of these reagents.

The process of our invention is preferably carried out such that at least one of the treatments with the non-nucleophilic strong base, the chiral amino alcohol, or the piperidine compound of formula (V) occurs in the presence of water or a $C_1$–$C_3$ alcohol (e.g., methanol), most preferably, water. The amount of water or $C_1$–$C_3$ alcohol used preferably ranges from 0.1 to 3.0 equivalents, more preferably 0.8 to 1.2 equivalents, most preferably 0.9 to 1.1 equivalents. The water or $C_1$–$C_3$ alcohol may be added to the tricyclic starting compound prior to, or simultaneously with, the addition of the base, the chiral amino alcohol, or the piperidine compound, or it may be added after any or all of these compounds are brought into contact with the tricyclic starting compound.

In a particularly preferred embodiment:
(a) 1.2 to 1.4 eq. of the non-nucleophilic strong base, preferably about 1.3 eq., are added to a solution containing:
 (i) the compound of formula (II),
 (ii) 1.1 to 1.3 eq. of the compound of formula (V), preferably about 1.2 eq., and
 (iii) 1.2 to 1.4 eq. of the chiral amino alcohol, preferably about 1.3 eq., while maintaining the temperature at 10° C. to 30° C., preferably 15° C. to 25° C.;
(b) the mixture from step (a) is cooled to 0° C. to 10 C., preferably 0° C. to 5° C. and 0.8 to 1.2 eq. of water, preferably about 1.0 eq. are added;
(c) an additional 0.9 to 1.1 eq. of the non-nucleophilic strong base, preferably about 1.0 eq. are added to the mixture from step (b) while maintaining the temperature at 0° C. to 10° C., preferably 0° C. to 8° C.; and
(d) the temperature of the mixture from step (c) is raised to 14° C. to 18° C., and an additional 1.1 to 1.3 eq. of the non-nucleophilic strong base, preferably about 1.2 eq. are added while maintaining the temperature at 14° C. to 18° C.

The process of our invention is economical, because the chiral amino alcohol can be recovered and recycled for further use. For example, after the reaction is judged to be complete by HPLC, the reaction mixture can be quenched by adding water, and stirred at a temperature of 0° C. to 5° C. to precipitate the chiral amino alcohol, which can be recovered by filtration.

The tricyclic starting compound of our process may be prepared by reducing a corresponding tricyclic ketone as depicted below:

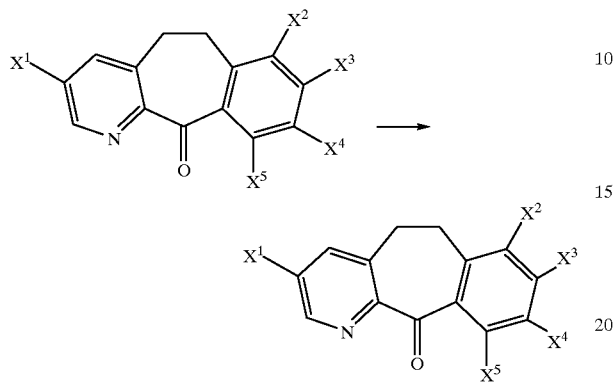

The reduction of the tricyclic ketone may be carried out by methods well known in the art. Preferably, the reduction is carried out by treating the tricyclic ketone with Zn and 2 equivalents of trifluoroacetic acid in a 2:1 mixture of tetrahydrofuran/acetic anhydride. The tricyclic ketone may be prepared according to methods known in the art, e.g., the methods described in PCT Publication Nos. WO97/23478, published Jul. 3, 1997, WO96/31478, published Oct. 10, 1996, WO96/30363, published Oct. 3, 1996, and WO95/10516, published Apr. 20, 1995. Alternatively, the tricyclic ketone may be prepared according to the following scheme:

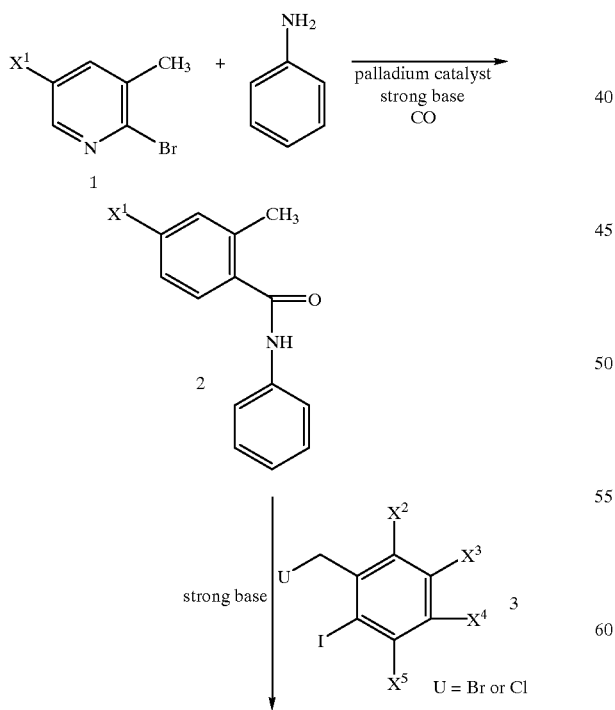

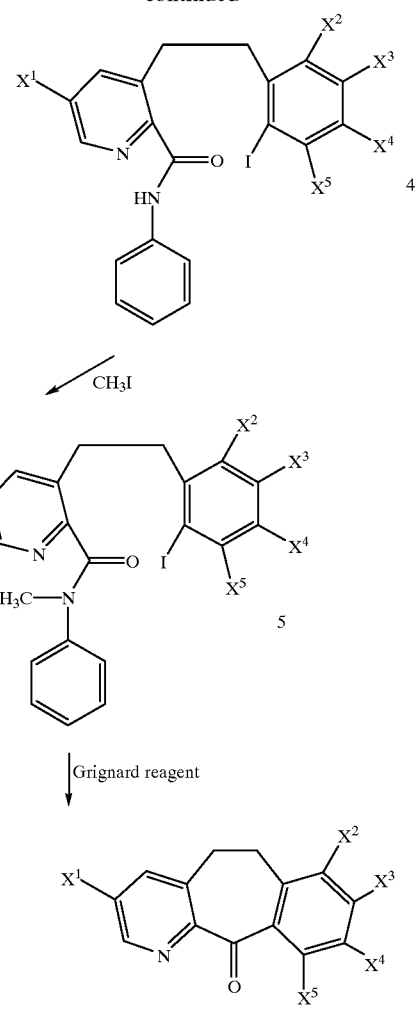

As shown in the scheme above, the pyridine compound 1 is reacted with aniline in the presence of a palladium catalyst, e.g., Pd(OAc)$_2$ or PdCl$_2$, carbon monoxide, a base, e.g., 1,8-diazabicyclo-[5.4.0]undec-7-ene ("DBU") or diisopropylethylamine, and an ether selected from ethylene glycol dimethyl ether, 2-methoxyethyl ether, and triethylene glycol dimethyl ether, to form amide compound 2. The reaction to form amide compound 2 is preferably carried out at a temperature of about 45° C. to 90° C., and a pressure of about 40 to 100 psi, in a suitable solvent, e.g., toluene or chlorobenzene. Amide compound 2 is reacted with an iodo-substituted compound 3 in the presence of a strong base, e.g., lithium diisopropylamide, in a suitable solvent, e.g., THF, to form compound 4. Compound 4 is reacted with CH$_3$I and a base, e.g., NaH to form methylated compound 5. Compound 5 is cyclized to form the desired ketone by reaction with a Grignard reagent, e.g., 2-methoxyphenylmagnesium bromide. Alternatively, the tricyclic ketone may be prepared according to the following scheme:

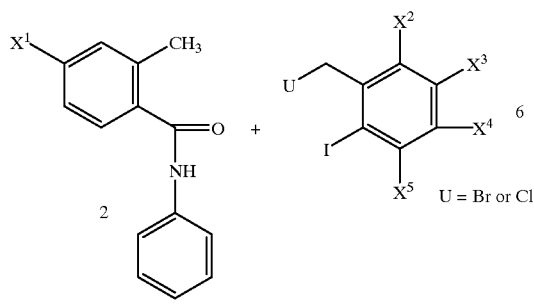

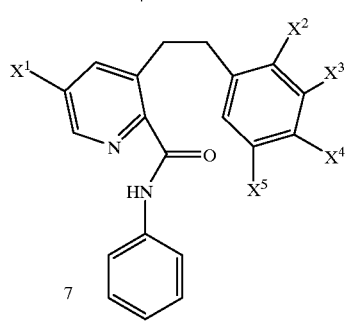

7

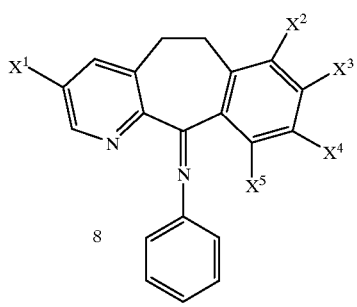

8

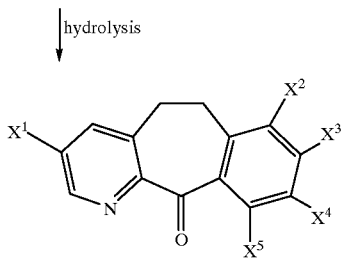

As shown in the scheme above, amide compound 2 is reacted with compound 6 in the presence of a strong base, e.g., lithium diisopropylamide, in a suitable solvent, e.g., THF to form compound 7. Compound 7 is cyclized by treating it with a dehydrating agent and a super acid, e.g., $P_2O_5/CF_3SO_3H$ or a dehydrating agent and a Lewis acid, e.g., $PCl_5/AlCl_3$ or $POCl_3/ZnCl_2$, and hydrolyzing the reaction product 8 to form the desired tricyclic ketone.

The norephedrine derivatives used in our process may be prepared by a one pot, two step process according to the following scheme:

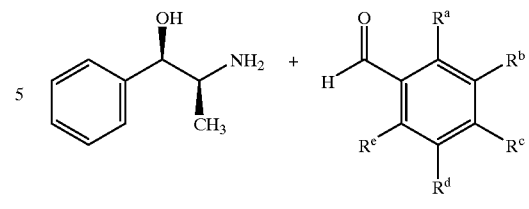

$R^a$, $R^b$, $R^c$, $R^d$, and $R^e$ = H, alkyl or alkoxy

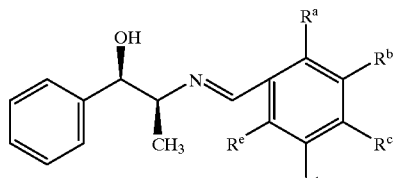

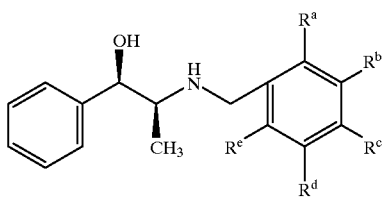

As shown in the scheme above, (1R, 2S)-(−)- norephedrine is reacted with an optionally substituted benzaldehyde by refluxing in ethanol, and reducing the product of that reaction with sodium borohydride at ambient temperature to produce the desired norephedrine derivative compound.

The quinine derivatives used in our process are either commercially available, or may be made from quinine or hydroquinine using methods known to those skilled in the art. (See, e.g., H. King, *J. Chem. Soc.* 1946, 523–524; and A. Renfrew, et al, *J. Am. Chem. Soc.* 1943, 65, 2309–2310.)

The following examples illustrate the foregoing invention, although such examples should not be construed as limiting the scope of the invention. Alternative reagents and analagous processes within the scope of the invention will be apparent to those skilled in the art.

Preparative Example A

One-pot, two step preparation of the Trimethoxybenzyl-Norephedrine Ligand

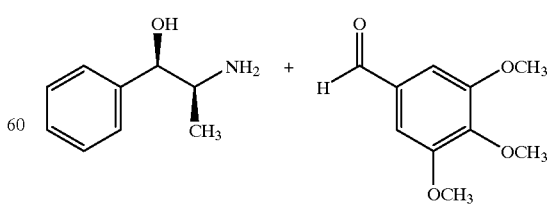

-continued

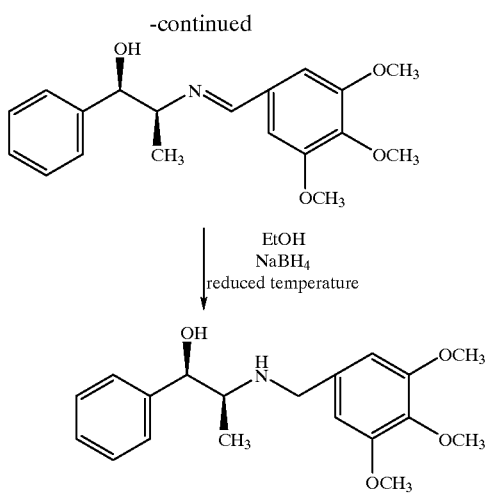

(1R,2S)-(−)-Norephedrine (100 g) and 3,4,5-Trimethoxybenzaldehyde (143 g) are dissolved in ethanol (1 L) and brought to a gentle reflux for 4 to 5 hours (average time required for completion). The reaction mixture is then cooled down in an ice-water bath, and sodium borohydride (37 g) is added portionwise. Reduction occurs overnight at room temperature. Once reduction is complete, the excess sodium borohydride is destroyed by adding water (25 mL). The organic solvent (ethanol) is then removed using a rotavap, and the product is extracted with ethyl acetate. Ethyl acetate is removed, using a rotoyap, leaving behind trimethoxybenzyl-norephedrine as a colorless oil.

Further purification is achieved by dissolving the trimethoxybenzyl-norephedrine oil in methanol (400 mL) and slowly adding aqueous hydrobromic acid 48% w/w (73 mL). A white solid precipitates which is filtered after 1 hour of stirring at room temperature. The ligand salt is recrystallized in a mixture of methanol/diethyl ether (12:1). The recrystallized salt is then freebased, using diluted aqueous sodium hydroxide, and extracted with toluene. The toluene is then removed with a rotovap, leaving behind trimethoxybenzyl-norephedrine (188 g) as a colorless oil.

$^1$H NMR (CDCl$_3$):δ7.33–7.24 (m, 7H); 6.55(s, 2H); 4.80 (d, J=3.8 Hz, 1H); 3.86–3.82(m, 9H); 3.00(dq, J=3.8 and 6.5 Hz, 1H); 1.39 (d, J=6.5 Hz, 1H); 0.9(d, J=6.5 Hz, 3H $^{13}$C NMR (CDCl$_3$): 154.3, 142.2, 138.2, 136.4, 129.1, 128.1, 127.1, 106.0, 74.4, 62.0, 59.1, 57.3, 52.7, 15.9.

Preparative Example B

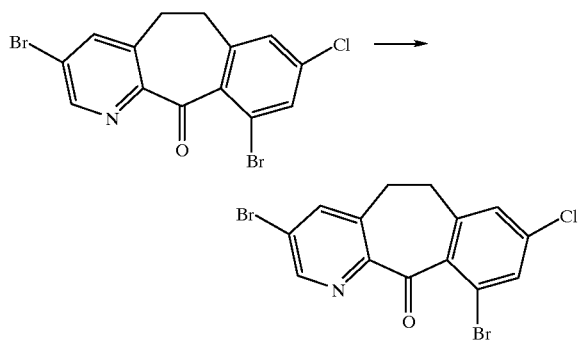

To a mixture of the tricyclic ketone shown above (40 kg, 1 eq.), acetic anhydride (72 L, 7.8 eq.) in THF (140 L) at −25° C. was added zinc dust (22.4 kg, 3.5 eq.) and then dropwise trifluoroacetic acid (16.8 L, 2.2 eq.) over a 2 hour period at −25° C. to −20° C. The mixture was slowly raised to room temperature over a period of 2 hours and kept at 18° C. to 20° C. over a period of 20 hours. Supercel (4 kg) and toluene (400 L) were added and the mixture was filtered. The extra zinc and inorganic residue were washed with toluene (80 L). The filtrate and wash were combined, and washed with water (200 L), 10% NaOH (160L×2) and water (200 L). After separating the organic layer from the aqueous layer, the organic layer was concentrated to 120 L. 2-Butanol (320 L) was added to the mixture, which was then concentrated to 120 L under vacuum. Again, 160 L of 2-butanol was added and the mixture was heated to reflux for 1 hour. The mixture was cooled down to 0° C. to 5° C. and stirred for 4 hours. The solid was filtered and washed with 80 L of 2-butanol. The crystalline product was dried under vacuum at 70° C. The yield was 32.6 kg (82%). Mp.: 163–1640° C. $^1$H NMR (CDCl$_3$), 8.38(d, J=2.0 Hz, 1H), 7.46(d, J=2.0 Hz, 1H), 7.44(d, J=2.0 Hz, 1H), 7.14(d, J=2.0 Hz, 1H), 4.54(s, 2H), 3.10–3.20(m, 4H). $^{13}$C NMR (CDCl$_3$): 154.1, 148.5, 143.9, 141.7, 137.2, 135.8, 133.9, 131.6, 128.7, 125.5, 119.8, 41.7, 32.9, 32.8.

If necessary, the product can be further purified by recrystallization from 7 volumes of 2-butanol and 1.5 volumes of toluene in 94% yield.

EXAMPLE 1

Chiral alkylation using a Norephedrine based ligand

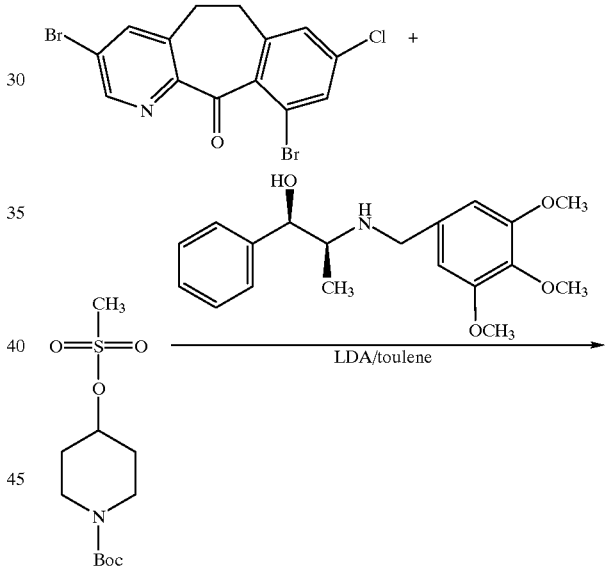

The trimethoxybenzyl-norephedrine ligand from Preparative Example A (76.8 g), the tricyclic methylene substrate from Preparative Example B (50 g) and mesylated N-protected piperidine derivative (43.2 g) are dissolved in toluene to a total volume of 1 L. The reaction mixture is then cooled down between 0° and −5° C. and lithium diisopropyl amide mono (tetrahydrofuran) solution (1.5 M in cyclohexane) ("LDA") (155 mL) is added, followed by the addition of water (2.1 mL). At this point, the temperature is maintained between 0° and −5° C. and the remaining LDA 1.5 M (172 mL) is added slowly over 4 to 5 hours. Once the reaction is completed, 1N hydrochloric acid (1.2 L) is added to precipitate out the chiral inducing ligand which is recovered by filtration and can be reused without any further purification. The aqueous layer is then separated from the organic layer (toluene) which contains the alkylated product (93–95% ee,>95% solution yield).

EXAMPLE 2

Using the procedure of Example 1, and substituting lithium 2,2,6,6,-tetramethyl piperidide for LDA, obtain the alkylated product (81% ee).

EXAMPLE 3

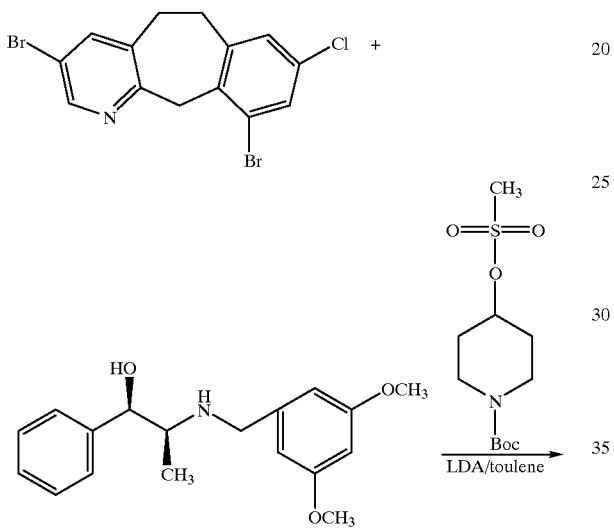

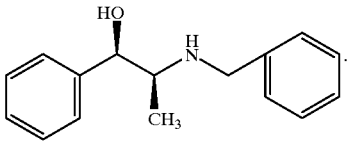

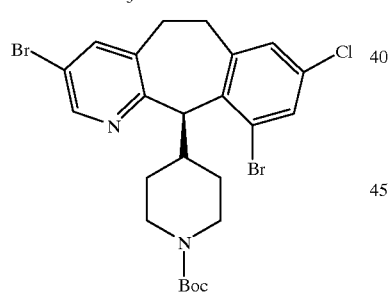

To a cooled (0 to 5° C.) solution of the norephederine derivative shown above (0.9 g) and the tricyclic compound (1.0 g) shown above dissolved in 40 mL of degassed toluene was added dropwise LDA 1.5 M (3.8 mL). The mixture is stirred at that temperature for 2 hours. A solution of the mesylated N-protected piperidine derivative shown above (1 g in 10 mL in toluene) is added to the reaction mixture. The reaction is allowed to return to ambient temperature. Monitor the reaction by HPLC to determine completion to obtain the alkylated product (57% ee).

EXAMPLE 4

Using the same procedure as Example 3, obtain the alkylated product (48% ee) by substituting the following norephederine derivative for the norephederine derivative used in Example 2:

EXAMPLE 5

Using the same procedure as Example 3, obtain the alkylated product (62% ee) by substituting 1,4-dilithium piperazide for LDA.

EXAMPLE 6

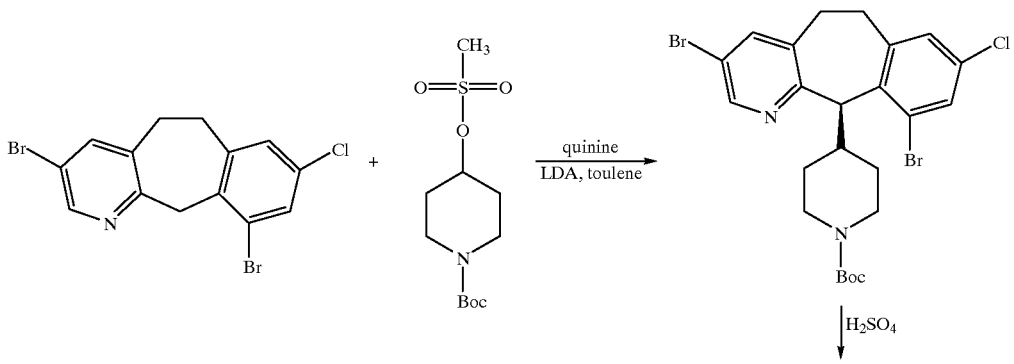

-continued

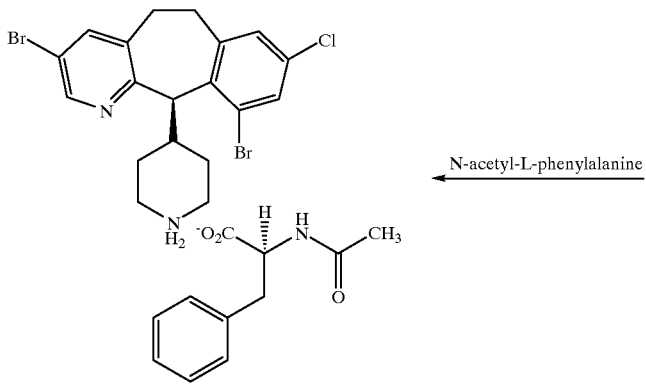

Mix the tricyclic compound (6.0 g) shown above and 4-mesyl-N-Boc-piperidine (5.0 g) in 150 mL toluene, heat to 40° C. for 30 minutes to obtain a clear solution, and cool to ambient temperature. Add the solution to a reaction flask containing solid quinine (6.0 g). Add 1.3 eq. of a solution of lithium diisopropylamide mono(tetrahydrofuran) (1.5 M in cyclohexane) ("LDA solution") slowly, while maintaining the temperature below 10° C., until the mixture turns red. Add $H_2O$ (1.0 eq.), stir for 10 minutes, and cool the reaction mixture below 5° C. Slowly add 1.0 eq. of the LDA solution, and warm the reaction mixture to 14° C. to 18° C. to obtain a clear solution. Add an additional 1.1 eq. of the LDA solution over a two hour period. Warm the resulting mixture to ambient temperature and stir for 18 hours. Quench the reaction mixture with 90 mL of 10% $H_2SO_4$. Remove the bottom aqueous solution. Add 24 mL of 20% $H_2SO_4$ to the toluene solution (organic top layer), heat to 85° C. for 4 hours, and cool down to ambient temperature. Add 15 mL of concentrated $NH_4OH$ to the reaction mixture and remove the bottom aqueous solution. Reduce the toluene solution (organic top layer) by vacuum distillation to a volume of 48 mL. Add 120 mL ethanol, and reduce by vacuum distillation down to a volume of 48 mL. Add a solution of 3.0 grams N-acetyl-L-phenylalanine in 120 mL ethanol, and subject the mixture to vacuum distillation to reduce the volume down to 48 mL. Stir at 70° C. for 1 hour, and cool to ambient temperature. Filter and wash the solid with a 1:1 solution of ethyl alcohol and methyl-t-butyl ether. Dry in a vacuum oven at a temperature of 55° C. for 18 hours to give 8.75 grams of the desired salt (80% molar yield, 96% purity, >98% e.e.).

$^1$H NMR of salt (CDCl$_3$): 8.45(s, 1H), 7.58(s, 1H), 7.52(s, 1H), 7.20 (m, 6H), 6.33(d, J=6Hz, 1H), 4.96(d, J=9Hz, 1H), 4.52(m, 1H), 3.55(m, 1H), 3.12–3.24(m, 5H), 3.0(m, 1H), 2.84(m, 1H), 2.58(m, 2H), 2.34(m, 1H), 2.00(s, 3H), 1.82(m, 1H), 1.62(m, 2H), 1.42(m, 1H).

$^1$H NMR of free base (CDCl$_3$): 8.45(s, 1H), 7.52(s, 1H), 7.48(s, 1H), 7.10(s, 1H), 4.88(d, J=9 Hz, 1H), 3.62(m, 1H), 3.25(m, 1H), 3.00(in, 3H), 2.78(m, 1H), 2.48(m, 2H) 2.25 (m, 1H), 1.50(m, 3H), 1.26(m, 2H).

EXAMPLE 7

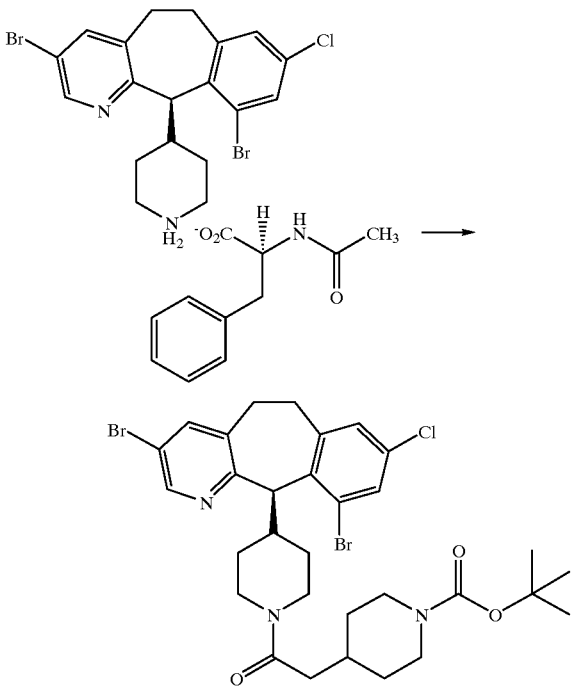

To a 500 ml round bottom flask equipped with a stirring bar, charge 10.0 g of (11R)-(8-chloro-3,10-dibromo-6,11 -dihydro-5H-benzo [5,6] cyclohepta [1,2-b] pyridin-11 -yl) -1 piperidine (S)-N-acetyl-L-phenylalanate, add 100 mL of toluene, 50 mL of 25% NaOH solution, and 100 mL of $H_2O$. Stir 30 minutes, add 1.0 g celite®, stir for an additional 5 minutes, then filter. Wash the celite® pad with 10 mL toluene. Separate the organic and aqueous layers and wash the organic layer with water (4×50 mL followed by 1×150 mL). Add 40 mL DMF, 0.199 g 1-hydroxybenzotriazole (HOBT), 3.19 g 1-(3-dimethylaminopropyl)-3-ethylcarbodiimide.HCl (EDCI.HCl) and 4.0 g of 1-N-tert -butoxycarbonylpiperidinyl-4-acetic acid and stir at room temperature until the reaction is complete (as judged by HPLC monitoring of the reaction). To the reaction mixture, add 50 mL of $H_2O$ and separate the organic and aqucous layers. Wash the organic layer with AcOH solution (0.1 mL AcOH/20 mL $H_2O$), 1×40 mL $H_2O$, NaOH solution (6.4 grams 24% NaOH/36 mL H₂O), 3×40 mL H₂O and then NaCl solution (3.9 grams/40 mL H₂O). Concentrate the organic layer to a volume of about 60 mL and chromatograph the toluene solution using 22.5 grams SiO₂ (Davison Grade 62), eluting with 1:1 EtOAc/toluene and collecting in 50 mL fractions. Analyze each fraction by thin layer chromatography and combine all fractions containing the product. Concentrate the combined fractions to about 50 mL, add 100 mL toluene and concentrate to about 100 mL. Add 3.5 grams alumina (basic, Activity I), stir for 30 minutes, filter and wash the alumina cake with 10 mL toluene. Repeat alumina slurry until HPLC indicates acceptable quality product. Concentrate toluene layer to about 20 mL, add 30 mL EtOAc, 60 mL heptane and allow to slowly cool to room temperature. After the product has precipitated, cool to 0° C. for one hour, collect the solid and wash with 30 mL 2:1 heptane/EtOAc. Dry the solid in a vacuum oven overnight to yield 7.98 g of product.

¹H NMR: (CDCl₃, δ): 8.42(s, 1H), 7.53(s, 1H), 7.50(s, 1H), 7.10–7.20(m, 6H), 6.36(d, 1H, J=7 Hz), 4.94(d, 1H, J=10 Hz), 4.48(m, 1H), 3.52(m, 1H), 3.24(m, 2H), 3.12(m, 3H), 2.98(m, 1H), 2.82(m, 1H), 2.53(m, 2H), 2.32(m, 1H), 1.98(s, 3H), 1.78(m, 1H), 1.56(m, 1H), 1.40(m, 1H).

Step B:

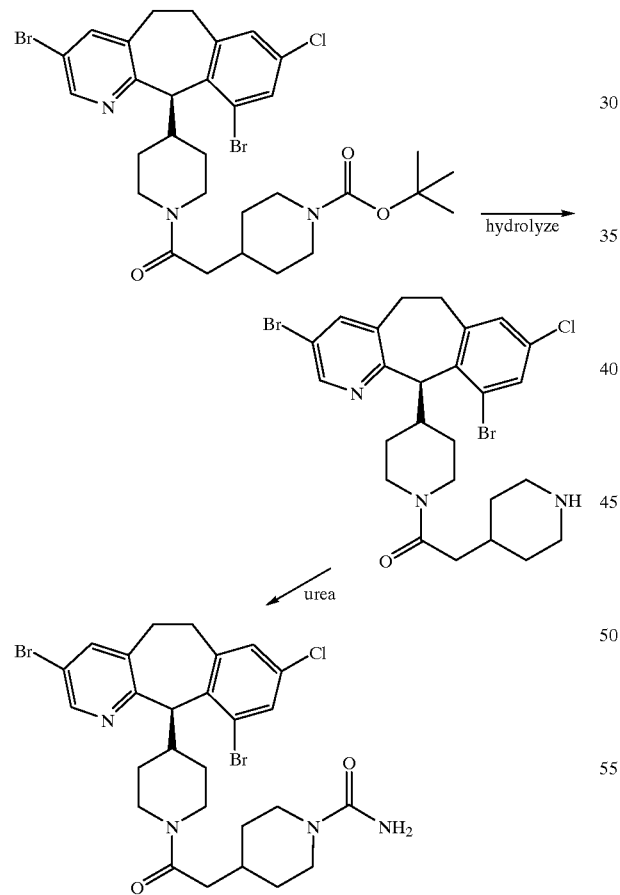

To a 250 mL round bottom flask equipped with a stirring bar, charge 7.07 g of the product from step A, above. Add 35 mL ethyl alcohol 2B, and stir. Cool the solution in an ice bath for 10 minutes, then add 42 mL of a 3 N HCl solution while maintaining the temperature below 25° C. Stir the reaction at room temperature until hydrolysis is complete (as judged by HPLC), typically 6 hours or longer. (If necessary, place reaction in a water bath, and stir at 50° C. for about 30 minutes to complete the hydrolysis.) Concentrate in a rotavap to about 35 mL, add 17.5 mL 1-methyl-2-pyrrolidinone, then adjust to pH 9 by slowly adding 3 N NaOH over a period of about 30 minutes, while avoiding solid formation by adjusting the rate of addition of the 3N NaOH. Add 28.0 g of urea, place in an oil bath heated to about 110° C., stir at mild reflux overnight to form a solid. Cool to about 50° C., then adjust to pH 6 using 3 N HCl. Collect the solid material, wash with 140 mL H₂O, and dry in a vacuum oven overnight to yield 5.434 g of product.

¹H NMR: (CDCl₃, δ): 8.38(d, 1H, J=8 Hz), 7.48(m, 1H), 7.43(s, 1H), 7.07(m, 1H), 7.07(m, 1H), 4.82(d, 1H, J=10 Hz), 4.54(m, 1H), 4.00(br s, 2H), 3.77(m, 1H), 3.56(m, 1H), 3.20(m, 1H), 2.90(m, 1H), 2.60–2.80(m, 3H), 2.30(m, 2H), 2.18(m, 2H), 1.90(m, 1H), 1.65(m, 2H), 1.38(s, 9H), 1.00–1.45(m, 7H).

Step C:

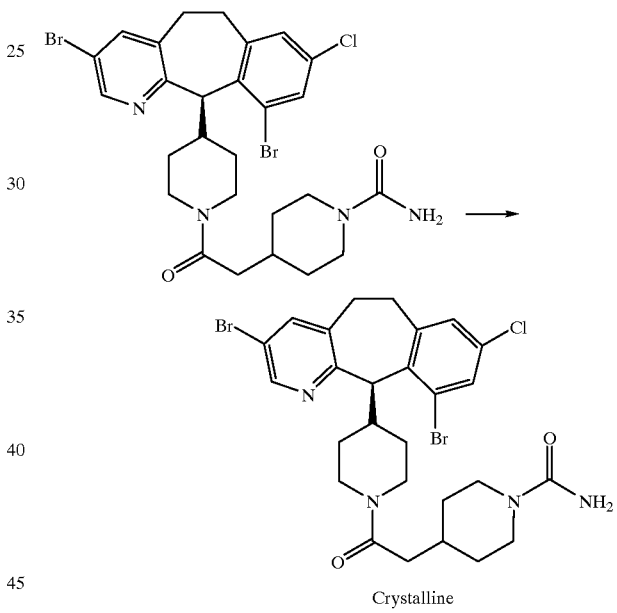

Crystalline

To a 500 mL round bottom flask equipped with a stirring bar, charge with 5.14 g of material from step B, above. Add 5 mL THF and 250 mL CH₂Cl₂. Stir at room temperature for about 30 minutes to dissolve all material to obtain a solution. Add 2.57 g of SiO₂, stir for 30 minutes, and then filter through a pad of celite. Wash with 15 mL of CH₂Cl₂, concentrate to about 50 mL, then add 100 mL THF and concentrate by distillation to 50 mL. Add 100 mL ethyl acetate and concentrate to 50 mL to form a white precipitate. Add 25 mL of ethyl acetate again, concentrate to about 50 mL, then cool to about 35° C. Filter, wash the solid with 15 mL cold ethyl acetate, and dry in a vacuum oven overnight to obtain 4.1187 g of product.

¹H NMR: (CDCl₃, δ): 8.42(s, 1H), 7.58(d, 1H, J=8 Hz), 7.50(s, 1H), 7.16(s, 1H), 4.92(d, 1H, J=9 Hz), 4.62(br s, 3H), 3.92(m, 3H), 3.62(m, 1H), 3.26(m, 1H), 3.00(m, 6H). 2.82 (m, 1H), 2.40(m, 2H), 2.22(m, 2H), 2.04(m, 1H), 1.78(m, 2H), 1.08–1.58(m, 6H).

EXAMPLE 8

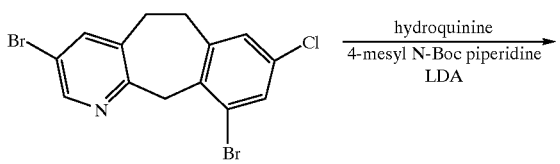

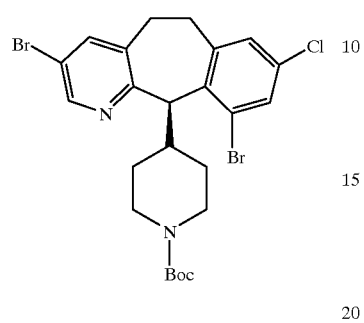

Mix the tricyclic compound shown above (0.207 g), hydroquinine (0.202 g) and 4-mesyl N-Boc-piperidine (0.204 g) in toluene (20×), stir at ambient temperature for 10 minutes, and cool to 0° C. Add 1 mL of lithium diisopropyl amide mono (tetrahydrofuran) solution (1.5 M in cyclohexane) ("LDA") slowly, while maintaining the temperature below 10° C. Warm the resulting mixture to ambient temperature and stir for 2 hours. HPLC analysis give 91.5% conversion and 68.5% ee.

EXAMPLE 9

Using the same procedure as Example 8, obtain the alkylated product (35% e.e.) substituting the following quinoline alchohol derivative for the hydroquinine used in Example

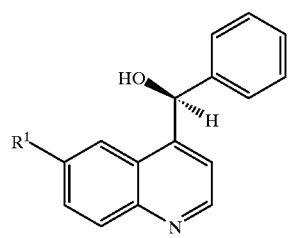

EXAMPLE 10

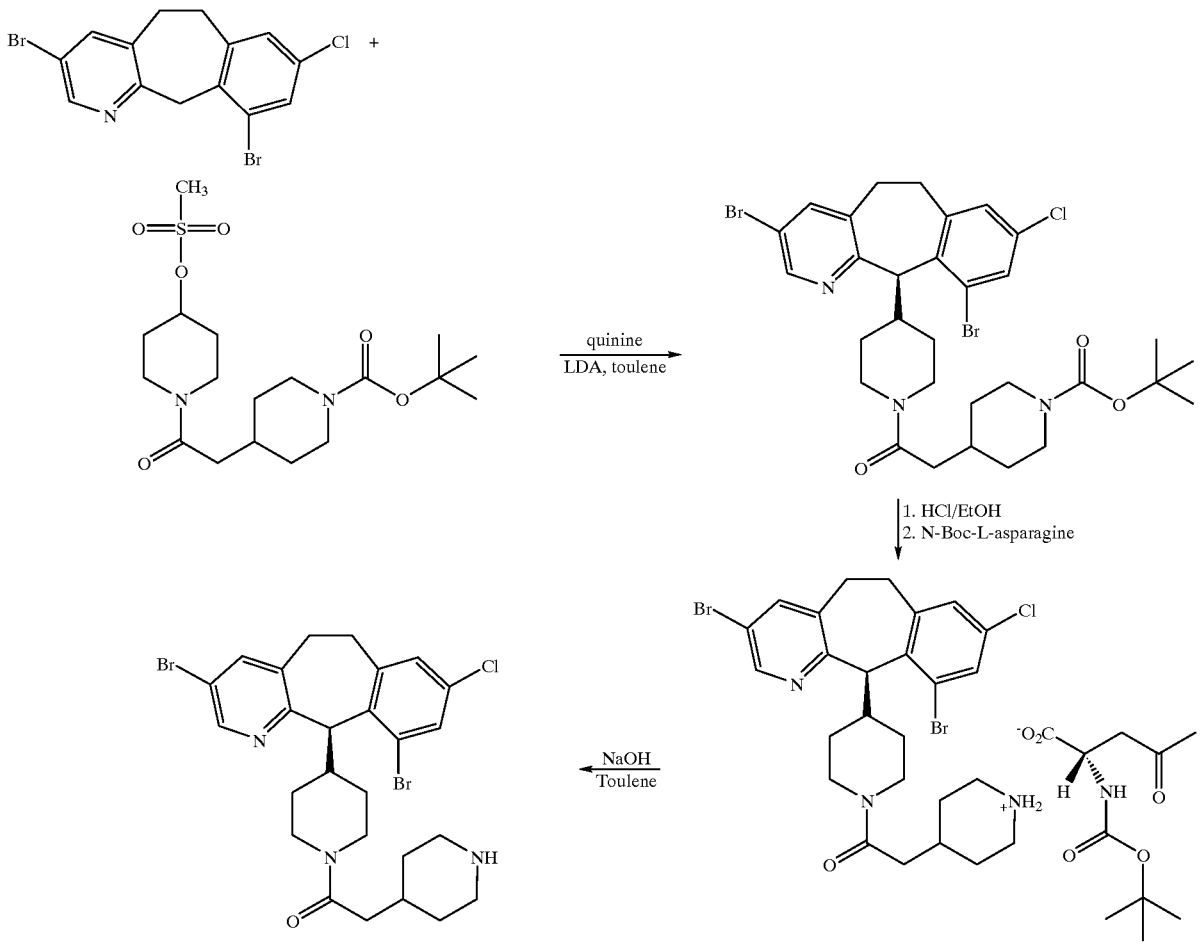

Mix the tricyclic compound (5.0 g) shown above and 4-mesyl-(1-[1,1-dimethylethoxy)carbonyl]-4-piperidinylacetyl)piperidine (6.3 g) in 125 mL toluene or anisole, heat to 40° C. for 30 minutes to obtain a clear solution, and cool to ambient temperature. Add, the solution to a reaction flask containing solid quinine (6.3 g). Add 1.5 eq of a solution of lithium diisopropylamide mono(tetrahydrofuran) (1.5 M in cyclohexane) ("LDA solution") slowly, while maintaining the temperature below 10° C., until the mixture turns red. Add H$_2$O (1.2 eq), stir for 10 minutes, and cool the reaction mixture below 5° C. Slowly add 1.2 eq of the LDA solution and warm the reaction mixture to 16 ° C. to 20 ° C. to obtain a clear solution. Add an additional 1.3 eq of the LDA solution over a five hour period. Stir the resulting mixture at ambient temperature for 18 hours. Cool the reaction to 0 ° C. and quench the reaction mixture with 20 mL water. Stir at 0 ° C. for 4 h and filter the quinine. Wash the organic phase with 1 N HCl. Separate the organic phase and reduce the toluene solution (organic top layer) by vacuum distillation to a volume of 45 mL, add 120 mL EtOH, and reduce by vacuum distillation down to a volume of 45 mL. Cool the solution in an ice bath for 10 minutes, then add 53 mL of a 3 N HCl solution while maintaining the temperature below 25 ° C. Stir the reaction at room temperature until hydrolysis is complete (as judged by HPLC), typically 6 hours or longer. (If necessary, place reaction in a water bath, and stir at 50° C. for about 30 minutes to complete the hydrolysis.) Concentrate in a rotavap to about 40 mL, add 120 mL toluene and 3 N NaOH until the pH of the aqueous is 12. Separate the toluene phase and reduce the toluene solution (organic top layer) by vacuum distillation to a volume of 40 mL. Add 120 mL isopropanol, and reduce by vacuum distillation down to a volume of 40 mL. Add a solution of 3.6 grams N-α-(tert-butoxycarbonyl)-L-asparagine in 80 mL isopropanol, and subject the mixture to vacuum distillation to reduce the volume down to 40 mL. Add 80 mL isopropyl acetate and heat at reflux for 3 h. Cool and stir for 1 hour at ambient temperature. Filter and wash the solid with 25 mL isopropyl acetate. Dry in a vacuum oven at a temperature of 55° C. for 18 hours to give the desired salt (98% ee). The solid salt is suspended in 100 mL of toluene, 50 mL of 25% NaOH solution, and 100 mL of H$_2$O. Stir 30 minutes, separate the organic and aqueous layers and extract the aqueous layer with toluene (2×10 mL). Extract the toluene solution with 25 mL 3 N HCl solution. The resulting aqueous solution may be treated with NaOH, 1-methyl-2-pyrrolidinone, and urea according to the procedure in Example 7 Step B to form the final compound formed in Example 7 Step B. If desired, other salts may be formed by replacing N-α-(tert-butoxycarbonyl)-L-asparagine in the foregoing method with Di-p-toluoyl-L-tartaric acid, N-(tert-Butoxycarbonyl)-L-proline, (S)-(-)-2-Hydroxy-3,3-dimethylbutyric acid, or (1R)-(+)-Camphanic acid.

EXAMPLE 11

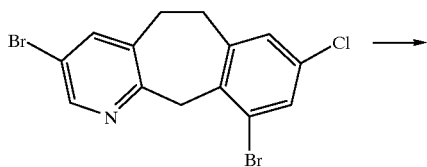

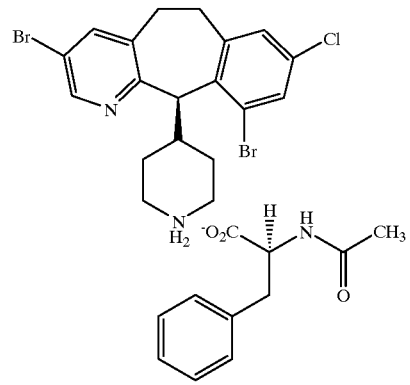

The following illustrates a batch preparation:

To a reactor charge 33 kg of quinine. In a separate reactor, charge 33 kg of the tricyclic compound shown above, 27.4 kg of 4-mesyl-N-Boc-piperidine, and 660 L toluene, heat to a temperature between 30° to 35° C. while agitating until all solids are dissolved, and slowly cool the solution to a temperature between 20° C. to 25° C. Add this solution to the first reactor containing the quinine and start agitating the mixture. Charge 165 L of toluene to the reaction mixture, and slowly charge 60.7 kg of lithium diisopropylamide mono(tetrahydrofuran) (1.5 M in cyclohexane) to the reaction mixture, while cooling the temperature to between 0° C. to 5° C. Charge 1518 mL water into the reactor, while maintaining the temperature between 0° C. to 5° C. While agitating, slowly charge 45.9 kg lithium diusopropylamide mono(tetrahydrofuran) (1.5 M in cyclohexane), while maintaining the batch temperature between 0° C. to 8° C. Slowly heat the batch to a temperature of 18±2° C., and agitate for a period of about 30 minutes at this temperature. Over a period of about 2 to 3 hours, charge 59.4 kg lithium diusopropylamide mono(tetrahydrofuran) (1.5 M in cyclohexane), while maintaining the batch temperature between 14±2° C. Agitate for about 12 hours at a temperature between 14±2° C. until the reaction is finished (confirm by HPLC). Charge 198 L of water to the batch and stir at a temperature between 0° C. to 5° C. for about 4 hours. Filter the batch and collect filtrate in a reactor. Wash the filter cake (recovered quinine) with 66 L of toluene followed by 66 L of water and combine the washings with filtrate in the reactor. Separate the lower aqueous phase from the organic phase. Wash the organic phase with 132 L of 7.6% aqueous sulfuric acid and separate phases to remove the lower aqueous phase. Add 198 L of 15% aqueous sulfuric acid to the batch while maintaining the reactor temperature below 80° C. Heat the batch and distill solvents from the solution until the batch temperature reaches about 85° C. and stop distillation and stir the reaction for about 4 hours at about 85° C. After cooling the batch to about 25 ° C., add 83 L of 25% ammonium hydroxide solution and agitate at a temperature between 20° C. to 30° C. Allow the batch to settle into layers and remove the lower aqueous layer. Cool the batch to a temperature below 20° C. Concentrate the batch by vacuum distillation to a final volume of about 264 L. Cool the batch to a temperature below 20° C., charge 627 L of ethyl alcohol, and concentrate the batch by vacuum distillation to a final volume of about 264 L, to remove toluene by solvent exchange. Cool the batch to a temperature between 20° C. to 25° C. Add a solution of 19.8 kg N-acetyl-L-phenylalanine in 495 L ethyl alcohol, heat the batch to a temperature between 55° C. to 60° C., while agitating for about 1 hour. Cool to a temperature of between 20° C. to 25° C. Subject the batch to vacuum distillation to reduce it to a final volume of about 264 L. Cool the batch to a temperature between 15° C. to 20° C., filter to recover the crystallized salt and wash with 52 L of a 1:1 solution of ethyl alcohol and methyl t-butyl ether. The washed crystals are dried for at least 16 hours at a temperature between 50° C. to 60° C. to produce 48 kg (84.4% molar yield) of product (101.4% purity; 98.8% ec).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

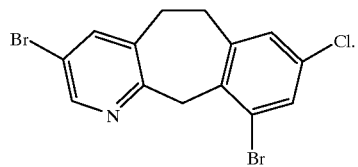

We claim:

1. A compound having the formula: